(12) United States Patent
Klatyk et al.

(10) Patent No.: US 9,388,053 B2
(45) Date of Patent: Jul. 12, 2016

(54) ANHYDROUS SODIUM CARBONATE HAVING A LOW PORE CONTENT

(71) Applicant: Merck Patent GmbH, Darmstadt (DE)

(72) Inventors: Jens Klatyk, Griesheim (DE); Hans-Kurt Peth, Alsbach-Haehnlein (DE); Thorsten Wedel, Stockstadt/Rhein (DE); Guenter Moddelmog, Reinheim (DE)

(73) Assignee: Merck Patent GmbH, Darmstadt (DE)

( * ) Notice: Subject to any disclaimer, the term of this patent is extended or adjusted under 35 U.S.C. 154(b) by 39 days.

(21) Appl. No.: 14/362,926

(22) PCT Filed: Nov. 10, 2012

(86) PCT No.: PCT/EP2012/004679
§ 371 (c)(1),
(2) Date: Jun. 5, 2014

(87) PCT Pub. No.: WO2013/083226
PCT Pub. Date: Jun. 13, 2013

(65) Prior Publication Data
US 2014/0336273 A1 Nov. 13, 2014

(30) Foreign Application Priority Data

Dec. 9, 2011 (EP) .................................... 11009721

(51) Int. Cl.
*C01D 7/07* (2006.01)
*C01D 7/00* (2006.01)
(Continued)

(52) U.S. Cl.
CPC . *C01D 7/07* (2013.01); *A61K 47/02* (2013.01); *A61K 47/08* (2013.01); *C01D 7/00* (2013.01);
(Continued)

(58) Field of Classification Search
CPC .............. C07D 7/07; C07D 7/00; C07D 7/12; C07D 7/35; A61K 47/02; A61K 47/08; C01P 2004/03; C01P 2006/10; C01P 2006/11; C01P 2006/12; C01P 2006/80; C01P 2006/82
See application file for complete search history.

(56) References Cited

U.S. PATENT DOCUMENTS 3,321,268 A * 5/1967 Copson .................... C01D 7/07 423/426
5,665,327 A * 9/1997 Warny ..................... C01D 7/35 423/421

(Continued)

FOREIGN PATENT DOCUMENTS

| CA | 2183952 A1 | 9/1995 |
|---|---|---|
| CN | 1142182 A | 4/2002 |

(Continued)

OTHER PUBLICATIONS

Official Action related to the corresponding Chinese Patent Application No. 201280060515.X dated May 20, 2015.
(Continued)

*Primary Examiner* — Jane C Osweck
(74) *Attorney, Agent, or Firm* — Millen White Zelano and Branigan, PC; John Sopp; Anthony Zelano

(57) ABSTRACT

The present invention relates to a highly pure, anhydrous sodium carbonate having a low pore content for use in pharmaceutical formulations and in the foods industry. Furthermore, a novel process for the preparation of this sodium carbonate is provided.

28 Claims, 2 Drawing Sheets

(51) Int. Cl.
*C01D 7/12* (2006.01)
*C01D 7/35* (2006.01)
*A61K 47/02* (2006.01)
*A61K 47/08* (2006.01)

(52) U.S. Cl.
CPC .. *C01D 7/12* (2013.01); *C01D 7/35* (2013.01); *C01P 2004/03* (2013.01); *C01P 2006/10* (2013.01); *C01P 2006/11* (2013.01); *C01P 2006/12* (2013.01); *C01P 2006/80* (2013.01); *C01P 2006/82* (2013.01)

(56) References Cited

U.S. PATENT DOCUMENTS

| | | | | |
|---|---|---|---|---|
| 5,788,947 | A | * | 8/1998 | Ruiz-Luna ............... C01D 7/35 423/420.2 |
| 5,792,473 | A | * | 8/1998 | Gergely ............... A61K 9/0007 424/466 |
| 6,710,050 | B2 | * | 3/2004 | Weibel ................. A61K 9/0095 424/465 |
| 2002/0010187 | A1 | | 1/2002 | Weibel et al. |
| 2004/0091523 | A1 | | 5/2004 | Weibel et al. |

FOREIGN PATENT DOCUMENTS

| | | | | |
|---|---|---|---|---|
| CN | 101712480 | A | | 5/2010 |
| CN | 101712480 | A | * | 5/2010 ............... C01D 7/35 |
| DE | 2926380 | A1 | | 1/1980 |
| DE | 670160 | T1 | | 3/1996 |
| GB | 2024187 | A | * | 1/1980 ............... C01D 7/37 |
| GB | 2024187 | A | | 1/1980 |
| JP | 46-26101 | B | | 7/1971 |

OTHER PUBLICATIONS

International Search Report from PCT/EP2012/004679 dated Feb. 25, 2013.

* cited by examiner

ANHYDROUS SODIUM CARBONATE HAVING A LOW PORE CONTENT

The present invention relates to a highly pure, anhydrous sodium carbonate having a low pore content for use in pharmaceutical formulations and in the foods industry. Furthermore, a novel process for the preparation of this sodium carbonate is provided.

PRIOR ART

Anhydrous sodium carbonate ("calcined soda") is employed for a multiplicity of industrial, pharmaceutical and food-technology processes and in a very wide variety of formulations. In these recipes, it has, inter alia, an alkalising action—but it is frequently also considered in the recipe development of "effervescent" preparations owing to its property of developing carbon dioxide liberation with dilute acids.

Various processes are known for the preparation of water-containing sodium carbonate. In these, the sodium carbonate is formed as deca-, hepta- or mono-hydrate. Anhydrous sodium carbonate is usually obtained by calcination or heating of the monohydrate.

The oldest process for the preparation of anhydrous sodium carbonate was developed by Leblanc in 1790. In this, the $Na_2CO_3$, CaS and carbon dioxide is obtained from sodium sulfate by heating with lime and coal. The sodium carbonate is separated off from the reaction product by leaching-out. Disadvantages of this process are the CaS and HCl formed as by-products and the high energy consumption. This process was superseded by the Solvay process, which was developed in 1861. In this, firstly ammonia and subsequently carbon dioxide is passed into a virtually saturated sodium chloride solution. This results in the formation of sparingly soluble sodium hydrogencarbonate. Heating of the separated-off sodium carbonate monohydrate gives the desired anhydrous sodium carbonate.

Owing to the low energy demand, it is increasingly preferred to obtain sodium carbonate from natural sources. Natural occurrences are known, for example, from Trona (USA), the large salt lakes in Egypt (Wadi Natrum) and North and South America. The desired anhydrous sodium carbonate is obtained therefrom by dissolution, purification and evaporation, or calcination processes.

Thus, the Japanese patent JP 46026101B4 discloses a process in which a sodium carbonate solution is prepared, to which NaOH is added. $CO_2$ gas is passed into the resultant solution. Vacuum evaporation gives a saturated solution, from which the monohydrate is in turn crystallised out when further NaOH is added. A disadvantage of this process is that on the one hand $CO_2$ gas must be passed in in order to achieve crystallisation-out of the monohydrate. On the other hand, separate calcination must be carried out after the separation in order to obtain the anhydrous sodium carbonate.

Anhydrous sodium carbonate is hygroscopic and is able to bind as much as 10% by weight of water from the environment without appearing moist. This results in re-formation of the monohydrate. This pronounced water-binding capacity of anhydrous sodium carbonate can result in stability problems in pharmaceutical recipes—in particular if moisture-sensitive substances are included. In addition, the water absorbed can result in discolouration reactions. However, a considerable problem arises through undesired evolution of carbon dioxide in the presence of acidic recipe components. In particular in so-called effervescent formulations, this premature evolution of carbon dioxide can result in a build-up of pressure in finished packaging and in destruction thereof ("bulges").

OBJECTIVE

The object of the present invention is therefore to provide an inexpensive process for the preparation of highly pure, anhydrous sodium carbonate which can be carried out simply in an energy-saving manner and which can provide a product which does not have the enumerated disadvantages, which is stable on storage and, owing to its morphological structure, has a lower tendency towards liberation of $CO_2$ in the presence of acids and which has lower hygroscopicity compared with commercially available anhydrous sodium carbonates

BRIEF DESCRIPTION OF THE INVENTION

It has been found that a synthetic preparation process gives a crystalline sodium carbonate which is distinguished by a particularly low water content and can therefore be designated as anhydrous and which has a particularly small surface area with a very low pore volume. It is apparent in SEM photographs that the anhydrous sodium carbonate prepared by the newly developed process has a particularly compact surface structure compared with conventional, commercially available anhydrous sodium carbonate. These novel properties result in improved compatibility with other, in particular with hydrolysis-sensitive, assistants and active compounds at the same time as significantly reduced hygroscopicity.

In particular, the anhydrous sodium carbonate is distinguished by the fact that it a) consists of particles having a smooth surface structure with a low pore content, b) has a BET surface area of less than 1 $m^2/g$, preferably less than 0.5 $m^2/g$, particularly preferably less than 0.2 $m^2/g$ and c) has a drying loss after preparation of not more than 0.2% by weight, preferably less than 0.15% by weight. Furthermore, it has a water vapour absorption capacity (WVAC) of <5% by weight at 60% relative humidity; <10% by weight at 70% relative humidity; <15% by weight at 80% relative humidity and <40% at 90% relative humidity. A sodium carbonate content of 99.5 to 100% was determined for the anhydrous sodium carbonate according to the invention by acidimetric determination. Thus, the user can be provided with a highly pure, anhydrous sodium carbonate which has significantly improved properties compared with conventional products, in particular if it is used for the preparation of pharmaceutical formulations.

In order to carry out the process according to the invention for the preparation of this novel anhydrous sodium carbonate having improved properties, an aqueous solution is prepared in which a) sodium hydrogencarbonate ($NaHCO_3$) and sodium hydroxide solution (NaOH) are dissolved in a molar ratio of 1:1 to 1:1.3 and b) sodium hydrogencarbonate and sodium hydroxide solution are dissolved in an amount such that the solution has a density in the range from 1.2 to 1.4 g/ml, preferably in the range from 1.25 to 1.34 g/ml, particularly preferably in the range from 1.28 to 1.31 g/ml, at 65° C., c) a catalytic amount of hydrogen peroxide and activated carbon are added successively to the solution, which is then filtered after adequate mixing, and d) the clear solution obtained is fed to a crystallisation apparatus, in which liquid is removed by vacuum evaporation at elevated temperature and a suspension density in the range from 1.54-1.86 g/ml, preferably 1.58-1.82 g/ml, particularly preferably in the range from 1.62-1.78 g/ml is set at which the crystallisation is carried out, e) the crystals formed are separated off by filtration, centrifugation or spinning-off and f) are introduced into a dryer at a temperature of in the range from 60-70° C. and are dried at a temperature 115 to 125° C. with continued mixing until the product obtained has a drying loss of not more than 0.2% by weight.

Good crystallisation results are achieved if the temperature during the crystallisation is set in the range from 50 to 95° C. and the density of the suspension is in the range from 1.54-1.86, in particular if the temperature is set in the range from 55 to 90° C. and the density of the suspension is in the range from 1.62 to 1.78 g/ml.

The crystallisation is preferably carried out in a loop crystalliser. In a particular embodiment, the crystals obtained from the crystalliser are fed to a screen centrifuge by means of a mixer screw, washed with water and introduced into a mixer dryer via a pneumatic dryer.

In a preferred embodiment, the crystals are fed to a fluidised-bed dryer via a screw conveyor and dried at a temperature in the range from 175 to 200° C., preferably in the range from 180 to 195° C., particularly preferably at 187° C., with an adequate residence time, that the product obtained has a drying loss of not more than 0.2% by weight.

Depending on the given prerequisites, the crystallisation can be carried out batchwise or continuously. The crystallisation is preferably carried out continuously, which enables more favourable crystallisation conditions to be utilised.

Anhydrous sodium carbonate prepared in accordance with the invention is particularly suitable for use in pharmaceutical preparations, in particular in ethical and OTC formulations. It can be employed in effervescent formulations, comprising vitamins and/or mineral substances and/or trace elements and/or hydrolysis-sensitive active compounds and results in improved properties of these products, such as, for example, improved long-term stability. The anhydrous sodium carbonate according to the invention is particularly suitable for use in effervescent formulations which comprise acidic active compounds and/or hydrolysis-sensitive active compounds, such as vitamin C or acetylsalicylic acid, since it has a substantially lower tendency to cleave off $CO_2$ in the presence of acidic additives or acidic active compounds. The anhydrous sodium carbonate according to the invention can be used both in the unmodified state and also in the modified state. Modified state can include modifications in the grain distribution, for example through screen fractionation or through grinding also modifications on the material surface, such as, for example, through the application of coatings and other manipulations. The improved properties have the advantage that formulations prepared have better long-term stabilities, and significantly less pressure build-up occurs in sealed packages, such as, for example, in medicament tubes, bags sealed in an air-tight manner or blister packs.

Due to these properties, the formulator in the pharmaceutical industry, in the foods industry or also in industrial sectors is provided with a material which improves the stability of his end product. In addition, the evolution of carbon dioxide in the presence of acids from formulations is slowed. This has, as already mentioned above, the consequence of improved storage stability of the packaged finished product.

Accordingly, the product prepared in accordance with the invention has particularly advantageous properties compared with commercially available products. This is a synthetically prepared highly pure, anhydrous sodium carbonate which meets the requirements of PhEur (Pharmacopoea Europaea), BP (British Pharmacopoeia), NF (USP/NF Compendiums) and has a content of not less than 99.5% by weight of sodium carbonate, and a drying loss of not more than 0.2% by weight. This content can be determined acidimetrically and is determined on dried substance. In particular, it is a product having a very low water content, which, although having a relatively coarse grain structure, also has, however, a significantly higher bulk and tapped density. The lower angle of repose of the product can be regarded as an indicator of an improved flow behaviour of the powder material. The evaluation of the SEM photographs of product samples shows that the sodium carbonate prepared in accordance with the invention has a significantly smoother crystal surface and thus a significantly smaller BET surface area than commercially available products, together with a significantly lower pore volume, as shown by the values of Examples 1 and 2 in Table 3. The latter can be determined by mercury intrusion.

The material exhibits significantly lower hygroscopicity than known sodium carbonate and has an extremely low water content immediately after preparation without a particular drying step. As measurements have shown, the water content immediately after preparation of the product is not more than 0.2% by weight, preferably lower than 0.15% by weight.

The product according to the invention has a smooth surface. SEM photographs show that it simultaneously has low porosity. Both result in a reduced water absorption capacity.

Various advantageous properties arise from this.

For example, the material reacts significantly more slowly in pharmaceutical formulations, in particular with hydrolysis-sensitive substances, and consequently has improved storage stability.

The delayed water absorption compared with conventional sodium carbonate delays the evolution of gaseous carbon dioxide, in particular in formulations comprising an acidic component, and thus prevents premature bulging, for example of blister packs, or the ejection of stoppers from tube packs.

In effervescent powders or effervescent tablets, the slowed reaction with the acidic recipe component, for example with citric acid, in water also achieves a slowing of carbon dioxide formation and thus prevents excessively vigorous foaming-over of the ready-to-drink solution.

Preparation Process:

To date, sodium carbonate has been prepared by a batch crystallisation. In accordance with the novel process according to the invention, the crystallisation can likewise be carried out batchwise, but the conditions are significantly more advantageous if the process, in contrast to conventional processes, is carried out continuously and in particular a continuous crystallisation is carried out. In this way, it is possible to allow the crystallisation to proceed under constant conditions, so that a product which is always the same is obtained. The preparation is preferably carried out continuously in a loop crystalliser. The preparation of corresponding products is described below and illustrated in greater detail by Examples 1 and 2 given. The examples given differ, in particular, through the type of final drying/calcination. It is basically a calcination under mild conditions, since this process step is carried out at fairly low temperatures. In this phase, the desired anhydrous sodium carbonate is formed from the sodium carbonate hydrate obtained primarily. In this connection, calcination under mild conditions means that elimination of water is carried out in accordance with the invention at temperatures from about 110 to about 200° C., depending on the design of the dryer and the desired drying time, while the calcination with elimination of water is usually preferably carried out at several hundred degrees, i.e. at 300 to 400° C. or more.

In order to carry out the process, an aqueous solution of highly pure sodium carbonate and sodium hydroxide solution is prepared. Sodium carbonate is crystallised out from this solution as monohydrate in a first step under suitable conditions. For this purpose, a mother liquor is prepared in which sodium hydrogencarbonate and sodium hydroxide solution are dissolved in a molar ratio of 1:1 to 1:1.3, preferably in a ratio of 1:1.1. This means that, in particular due to a slight excess of sodium hydroxide solution, improved crystallisation-out can be achieved.

In order to accelerate the reaction

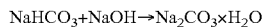

$NaHCO_3 + NaOH \rightarrow Na_2CO_3 \times H_2O$ a relatively small amount of $H_2O_2$ solution (30%) is added to the reaction mixture, more precisely it has been found that addition in the ratio sodium hydrogencarbonate/sodium hydroxide solution to $H_2O_2$ solution (30%) in the range from 700:1 to 900:1, preferably 800:1 to 760:1 particularly preferably 780:1, based on the weight of the entire solution, is particularly advantageous. The solution is heated for a few minutes, preferably 10 to 15 minutes, with stirring and, for further processing, re-cooled to a suitable temperature in the range from 50 to 70° C. This solution is allowed to rest for a few hours until the reaction is complete. After about 6 to 10 hours, preferably after 8 hours, the solution can be processed further. After the rest time, activated carbon in a weight ratio of sodium hydrogencarbonate/sodium hydroxide solution to activated carbon in a ratio of 20000:1 to 10000:1, preferably 16500:1 to 14000:1, particularly preferably 15600:1, based on the weight of the entire solution, is added to the resultant solution, and mixed vigorously. After adequate mixing with stirring, the solution is filtered using a suitable device, preferably using filter equipment which contains fine filters having a pore width of 1 μm.

Due to the amount of sodium hydrogencarbonate and sodium hydroxide solution dissolved in the solution, the solution has a density in the range from 1.2 to 1.4 g/ml, preferably in the range from 1.25 to 1.34 g/ml, particularly preferably range in the 1.28 to 1.31 g/ml, at 65° C.

This filtered, clear solution is fed to the crystallisation apparatus. This is preferably a heatable loop crystalliser with fill level control in which the solution can be stirred and can be pumped around by means of a pump. In particular, it is possible to place the crystalliser under vacuum so that the crystallisation can be carried out continuously with vacuum evaporation. In order to carry out the crystallisation, a suspension density in the range from 1.54-1.86 g/ml, preferably 1.58-1.82 g/ml, particularly preferably in the range from 1.62-1.78 g/ml, becomes established due to evaporation of water, depending on the temperature set. As described in Example 1, a suspension density of 1.62-1.78 g/ml becomes established at a temperature in the range from 70-90° C. and a pressure of about 67 mbar. In order to obtain a homogeneous product and in order to be able to achieve a constant product yield, it is important to ensure that the suspension density is maintained while the crystallisation is carried out and the temperature is in the pre-specified range. Optimum results are obtained under these conditions if the suspension density during the crystallisation is 1.70 g/ml and the temperature is held at 80° C.

In order to carry out the crystallisation continuously, preprepared hydroxide solution which has a suspension density of about 1.28-131 g/ml at 65° C. and has been pre-treated with $H_2O_2$ solution, activated carbon and by filtration like the solution originally employed is replenished continuously.

If the crystallisation is carried out at lower temperature, the suspension density should be set to a higher value. If, for example, the crystallisation is carried out at temperatures in the range from 50 to 60° C., preferably at 55° C., the density of the suspension solution should if possible be set in the range from 1.72-1.75 g/ml. However, it is in any case advisable to maintain a suspension density in the range from 1.62-1.78 g/ml in order to be able to ensure rapid separation-off of the crystals.

In accordance with the continuous performance of the process, the mother liquor is circulated and topped up continuously with sodium hydrogencarbonate and sodium hydroxide solution and, as described above, pre-treated, before the solution is re-employed for crystallisation. However, it is also possible to top up in part with corresponding freshly prepared solution, so that batches with addition of mother liquor in an amount of 0 to 100%, based on the entire solution, are crystallised.

The crystals forming are separated off from the solution by suitable devices by means of filtration, centrifugation or spinning-off. For example, the crystal slurry formed can be pumped by means of a mixer screw to a screen centrifuge (4-stage scraper screw with 0.25 mm screen insert), where the product is washed with a little water and introduced into a mixing dryer via a pneumatic dryer. The product obtained is dried for at least 10 hours with continuous mixing, and the monohydrate is converted into the desired anhydrous sodium carbonate. The mixing dryer used is for this purpose filled with about 1000 kg of moist, crystalline sodium carbonate, and the heating power is set so that a temperature in the range from 115 to 125° C. becomes established. The drying is complete when the product obtained in the form of anhydrous sodium carbonate has a drying loss of not more than 0.2% by weight, preferably less than 0.15% by weight. In the case of the product amounts initially introduced in the mixing dryer, this is the case after about 10 hours.

Instead of in a mixing dryer, the subsequent drying with formation of anhydrous sodium carbonate can also be carried out in a fluidised bed. A fluidised bed of this type can have various designs known to the person skilled in the art. In order to carry out Example 2 reproduced in this description, a 3-zone fluidised-bed dryer was employed.

In Example 1 described, the drying is carried out in a heatable mixing dryer in vacuo (vacuum dryer). The dryer is a commercially available cone-and-screw dryer. Owing to the dimensions of the dryer and its design, uniform heat exchange and continued product mixing during drying are ensured. In the vacuum dryer, the drying is carried out at about 20 to 60 mbar, preferably at 35 to 45 mbar. The drying temperature in the range from 115 to 125° C. is regulated during the drying operation by means of indirect steam heating at about 4 bar. Due to the application of a vacuum, particularly gentle drying occurs in a shortened drying time. Other mixing dryers of different design, which serve the same purpose and can preferably be operated continuously, can also be employed for this purpose.

In contrast to the situation described in Example 1, the final drying in Example 2 is carried out, by contrast, in a fluidised bed using hot air, to be precise in such a way that a temperature in the range from 175 to 200° C. becomes established. The drying is preferably carried out at a temperature in the range from 180 to 195° C. In the specific embodiment of Example 2, a temperature of 187° C. becomes established. At this temperature, a product having the improved properties outlined is obtained, as shown in the following tables for the product of Example 2. The fluidised bed employed for carrying out Example 2 is a 3-zone fluidisedbed dryer having a length of 4550 mm, a width of 450 mm, a weir in the 1st zone of 130 mm and an outlet-side weir having a dimension of 200 mm. Fluidised-bed dryers having other dimensions and designs can also be employed for drying the crystals, but it is essential, both in the case of drying in the mixer dryer and also in the fluidised-bed dryer, that the drying and calcination can be carried out in one step at relatively gentle temperatures and with continued mixing. This is accomplished in the fluidised-bed dryer by the constant swirling of the crystalline product particles in the hot gas stream which takes place during the drying.

After cooling of the product in the cooling zone at a temperature of about 24° C., an anhydrous sodium carbonate which has a drying loss of not more than 0.2% by weight is obtained as product. The product preferably has a drying loss of less than 0.15% by weight with a sodium carbonate content of not less than 99.5% by weight. Especially for a product which has been prepared in accordance with the description of Example 2, the sodium carbonate content, determined acidimetrically, is in the range from 99.6-99.7% by weight.

Anhydrous sodium carbonate prepared in accordance with the invention has particularly advantageous properties for further processing to give pharmaceutical formulations. As shown by Examples 1 and 2 given, products according to the invention have bulk densities in the range from 1.050 to 1.140 g/ml, and have a tapped density in the range from 1.18 to 1.30 g/ml. Furthermore, angles of repose of the products prepared in accordance with the invention are in the range from 30.0° to 31.5°, meaning that they can be processed particularly well or, if necessary after prior grain fractionation by sieving or grinding, can be employed in pharmaceutical preparations in the form of solid pharmaceutical formulations, such as tablets, capsules, powders, granules or capsules for oral use. In these, they can again be processed particularly well with acidic additives and active compounds.

Conditions for Preparation:

The conditions for preparation of the product according to the invention arise from the following preparation description in Examples 1 and 2. The product properties arise from the measured physical characterisation data, which are summarised in Tables 1 to 6.

Product Properties and Determination Thereof

The properties of the highly pure sodium carbonate described here in the use as tableting assistant and as constituent in pharmaceutical formulations is determined, in particular, by the size of the particles, their structure and surface nature, but also by the water content. In order to have a storable product which liberates as little $CO_2$ as possible, it is important to prepare a product with the lowest possible water content. For the production of tableted products from the sodium carbonate described, the bulk density, the tapped density and the angle of repose are of considerable importance. In order to be able to produce products which repeatedly remain the same over time and to be able to compare the properties of this starting material, the same determination methods should always be employed. Standardised methods for the determination of the various product properties are therefore also employed in the present case for assessment of the properties.

1. The determination of the bulk density is carried out in accordance with DIN EN ISO 60: 1999 (German version); data in the tables as "g/ml",
2. The determination of the tapped density is carried out in accordance with DIN EN ISO 787-11: 1995 (German version)—data in the tables as "g/ml"
3. The determination of the angle of repose is carried out in accordance with DIN ISO 4324: 1983 (German version); data in the tables as "degrees"
4. The surface area is determined by the BET method and the procedure and evaluation are carried out as described in the reference "BET Surface Area by Nitrogen Absorption" by S. Brunauer et a. (Journal of American Chemical Society, 60, 9, 1983), where the measurements is carried out using the instrument: ASAP 2420 from Micromeritics Instrument Corporation (USA) under nitrogen. The determination is carried out using a sample weight of 3.0000 g and drying by heating at 50° C. (10 h). The values indicated are the arithmetic mean of three determinations.
5. The determination of the pore volume is carried out by mercury intrusion using an instrument from CE INSTRUMENTS (PASCAL 400), in a pressure range from 0-70 atm for pores having a diameter of 200000-2000 Å and in a pressure range from 70-2000 atm for pores having a diameter of 2000-36 Å using samples having a sample weight of about 100 mg.
6. The particle size determination is carried out either
    a) via laser diffraction with dry dispersion using the Mastersizer 2000 instrument with the Scirocco 2000 dispersion unit from Malvern Instruments Ltd. (UK). The determinations are carried out at a counter-pressure of 1, 2 and 3 bar; evaluation by the Fraunhofer method; evaluation model: general purpose; refractive index 1.000; obscuration: 7-20%; measurement time (snaps or ms) 7500; feed rate: 100%. The measurement is carried out in accordance with ISO 13320-1 and in accordance with the information in the technical manual of the instrument manufacturer; data in % by vol.
    or
    b) via laser diffraction with wet dispersion using the Mastersizer 2000 instrument with the Hydro 2000S wet-dispersion unit from Malvern Instruments Ltd. (UK) The dispersion medium used is ethanol, denatured with 1% of ethyl methyl ketone (Art. No. 1.00974 Merck KGaA, Germany); refractive index 1.360; obscuration; 10-20%; measurement time (snaps or ms) 7500; stirrer speed 2000 rpm; no ultrasound performance. Before the measurement, the sample is pre-dispersed in the measurement cell for 3 minutes with stirring at 2000 rpm. The measurement is carried out in accordance with ISO 13320-1, and corresponding information in the instrument manufacturer's technical manual; data in % by vol.;
    or
    c) by dry sieving via a screen tower: Retsch AS 200 control from Retsch (Germany). For performance, an amount of substance of about 200.00 mg is weighed out; the sieving time: 30 minutes; intensity: 1 mm; interval: 5 seconds. Analytical screens with metal wire mesh in accordance with DIN ISO 3310; screen widths (in μm): 710, 600, 500, 400, 355, 300, 250, 200, 150, 100, 75, 50, 32 are used. The data of the amount distribution per screen fraction is indicated in the tables as "% by weight of the sample weight".
7. In order to determine the content, 1 g of material are dissolved in 50 ml of water and titrated rapidly with HCl (1 mol/l) against Methyl Orange. After the colour change, the solution is heated at the boil for two minutes, cooled and, if necessary, again titrated to the colour change.

1 ml of hydrochloric acid (1 mol/l) corresponds to 0.052995 g of sodium carbonate. The content is calculated on dried substance.

The basic procedure for the determination is described in the specialist literature, such as, for example, in G. Jander, K. F. Jahr, H. Knoll "Maβanalyse—Theorie und Praxis der klassischen und der elektrochemischen Titrier-verfahren" [Volumetric Analysis—Theory and Practice of Classical and Electrochemical Titration Methods], Verlag Walter de Gruyter, 1973 ISBN 3 11 005934 7

8. The drying loss is determined by weighing out 2 g of substance accurately and drying at 300° C. for at least two hours, i.e. to constant weight. The weight loss is quoted in % by weight.
9. SEM photograph conditions: LEO 1530 instrument (Carl Zeiss, Oberkochen, Germany)
10. FCD 050 sputter coater (Balzers Union, Liechtenstein) or EMITECH K575 (EM Technologies, Ashford (Kent), England). The samples are fixed using a conductive tab and sputtered with platinum in argon atmosphere.
11. TGA conditions: instrument: Auto TGA 2950 HR V5.4A, method: 20K/min., res. 3, sens. 5→500, 74 ml of $N_2$/min., Pt crucible; weight loss quoted in % by weight; measurement carried out in accordance with manufacturer's instructions.
12. DVS conditions: Surface Measurement Systems Ltd. UK 1996-2000, method: 0-98%, 10% steps, 25° C., 0.0005% min., half cycle.sao; measurement carried out in accordance with manufacturer's instructions
13. Density determinations: in general by tuning fork measurements, for example using instruments from Anton Paar GmbH/Austria; exception: the density determination in the crystalliser is carried out by a Coriolis mass flow meter, for example from Endress+Hauser Messtechnik GmbH+Co. KG/Germany. All measurements are carried out in accordance with the instrument manufacturer's procedure descriptions.

The present description enables the person skilled in the art to apply the invention comprehensively. Even without further comments, it is therefore assumed that a person skilled in the art will be able to utilise the above description in the broadest scope.

Should anything be unclear, it goes without saying that the cited publications and patent literature should be consulted. Accordingly, these documents are regarded as part of the disclosure content of the present description.

For better understanding and in order to illustrate the invention, two examples are given below which are within the scope of protection of the present invention. These examples also serve to illustrate possible variants. Owing to the general validity of the inventive principle described, however, the examples are not suitable for reducing the scope of protection of the present application to these alone.

Furthermore, it goes without saying to the person skilled in the art that, both in the examples given and also in the remainder of the description, the component amounts present in the compositions always only add up to 100% by weight or mol-%, based on the entire composition, and cannot exceed this, even if higher values could arise from the percent ranges indicated. Unless indicated otherwise, % data are therefore % by weight or mol-%, with the exception of ratios, which are reproduced in volume figures.

The temperatures given in the examples and description and in the claims are always in ° C.

EXAMPLES

Example 1

Reaction:

Chemicals:

| Sodium hydrogencarbonate | 23.8 kmol; 2000 kg of aqueous solution |
|---|---|
| | 45% sodium hydroxide solution 25.9 kmol, 2300 kg of aqueous solution |
| Activated carbon | 0.5 kg |
| Hydrogen peroxide (30%) | 10 l |
| DI water | 3500 l |

Product yield: sodium carbonate, anhydrous≈1250 kg (about 47% of theory)

The following apparatuses are necessary for the procedure:
1 raw materials addition station
2 batch tanks 10000 l
1 Scheibler filter
2 guard filters
2 high-purity filtrate tanks 10000 l
1 loop crystalliser 6300 l
1 condensate tank
2 mother-liquor collection tanks 5000 l
1 screen centrifuge
1 conveying screw
1 rinse-water collection tank 500 l
1 flow dryer
1 cyclone
1 filter bunker
1 mixing dryer 2500 l
2 conveying-device fillers
1 waste-air scrubber
2 waste-water tanks 10000 l Before commencing preparation of the product, the plant parts are connected to one another in a suitable manner, taking into account effective waste-air treatment. Since sodium carbonate, sodium hydrogencarbonate and sodium hydroxide solution are slightly water-polluting (WHC 1), the waste-air treatment plants, scrubbers and filters are monitored via particle measurement in the waste-air stream. The maximum allowable amount of substance in the waste-air stream is 20.00 mg/m³.

Procedure:

Once-only preparation (preliminary batch) of a mother liquor: about 3500 l of cold DI water (deionised water) or condensate are initially introduced in the batch reactor. The stirrer is switched on. 1550 l of sodium hydroxide solution (45%), and subsequently slowly 2000 kg of sodium hydrogencarbonate are subsequently introduced successively (duration: about 2 hours owing to considerable evolution of heat). The batch is heated at about 80° C. for about 10 minutes. About 10-15 l of hydrogen peroxide (30%) are then added. The mixture is subsequently re-cooled to 65° C. At the end, the solution has a density of about 1.28-1.31 g/ml at about 65° C. This setting must be checked! The subsequent standing time of the batch must be at least 8 hours.

Subsequent Batches:

The mother liquor obtained from the preliminary batch is initially introduced. 1050 l of sodium hydroxide solution (45%) are added with stirring. 1500 kg of sodium hydrogencarbonate are slowly introduced over the course of one hour, and the mixture is made up to 8000 l with DI water, and 12.5 l of hydrogen peroxide (30%) are added, and the mixture is heated at the boil for 10 minutes. The batch is cooled to 65° C. At this temperature, the solution should have a density of 1.28-1.31 g/ml. The standing time of the batch must likewise be at least 8 hours.

After the rest time, the solution is filtered using the filter unit provided (fine filter 1.0 μm filter) after addition of activated carbon, so that a clear solution is obtained.

For crystallisation, the crystalliser is filled and the stirrer, circulating pump and vacuum pump switched on (ensure optimum setting). The bottom heating and the central heating circuit activated, and the steam valves on the heat exchanger opened.

The sodium carbonate solution is fed to the loop crystalliser with fill level control and crystallised continuously. During the crystallisation, a suspension density in the range from 1.62-1.78 g/ml and a crystallisation temperature of in the range from 70-90° C. must be maintained. The condensate is disposed of instead of DI water in tanks provided for this purpose. During the crystallisation, optimum target-value setting must be ensured.

Stirrer speed≈60 rpm
Tank pressure≈67 mbar
Fill level≈45%
Density 1.70 g/ml (temperature: 80° C. optimum setting)

In order to carry out the crystallisation continuously, pre-prepared hydroxide solution which has a density of about 1.28-1.31 g/ml at 65° C. and has been pre-treated like the mother liquor originally used must be correspondingly replenished continuously.

Testing of the Hydroxide Solution Employed for the Crystallisation:

In order to check the settings, 20 ml of barium chloride solution (10%) are initially introduced in a clean beaker. 2 ml of the batch solution used for the crystallisation are then added to this barium chloride solution.

After addition of 5 drops of phenolphthalein solution, the solution becomes a red colour. The solution is slowly titrated with 0.1 N hydrochloric acid until the colour disappears. The consumption of hydrochloric acid must be between 6.0 and 7.0 ml. If necessary, the batch is corrected as follows:

The batch solution is brought to a temperature of 40° C. by means of water cooling.

In the case of a consumption >7.0 ml, sodium hydrogencarbonate is added.

In the case of a consumption <6.0 ml, sodium hydroxide solution is added.

The crystal slurry formed is pumped to a screen centrifuge (4-stage scraper screw and 0.25 mm screen insert) by means of a mixer screw, and the product is washed with ≈55 l/h of DI water.

The moist product introduced into the mixing dryer via a flow dryer (waste-air temperature in the range from 60-70° C.) in such a way that the mixer is filled with about 1000 kg of sodium carbonate.

The product is dried in the mixer dryer for 10 hours using 4 bar of indirect steam heating, where a final temperature of about 115-125° C. becomes established at 40 mbar vacuum. The product is subsequently cooled to 30° C. The cooling takes about 3 hours. The drying loss of the product must not be higher than 0.2% by weight.

The mother liquor is circulated and topped up with≈1500 kg of sodium hydrogencarbonate and about 1050 l of sodium hydroxide solution (45%), and the remainder of the procedure is carried out as described under "subsequent batches". Batches with mother liquor of 0-100% can be carried out.

Example 2

The crystals are prepared as described under Example 1, but the crystallisation is now carried out at about 55° C. and a density of 1.72-1.75 g/ml and introduced into a 3-zone fluidised-bed dryer (for example from Vibra Maschinenfabrik Schultheis GnbH & Co. KG/Germany or Hosokawa Micron Group/Japan) via a screw conveyor and dried to give anhydrous sodium carbonate. (The fluidised bed here has a length of 4550 mm and a width of 450 mm, the weir in zone 1 has a height of 130 mm and the outlet weir has a height of 200 mm.) The drying in the fluidised bed is carried out in zones 1 and 2 at 187° C. with a subsequent cooling zone at 24° C. The amount of air employed in zones 1 and 2 is 890-910 m³/h with a mass throughput of product of 2000 to 6000 l/d (liters per day). The temperature of the feed air and the residence time of the material in the plant must be selected so that the end product after leaving the fluidised-bed dryer has a maximum drying loss of 0.2% by weight.

The drying of the monohydrate in the fluidised-bed dryer enables the in continuous preparation of an anhydrous sodium carbonate which has a content of 99.6-99.7% of sodium carbonate.

Comparison of the Properties of the Anhydrous Sodium Carbonate from Examples 1 and 2 Prepared in Accordance with the Invention with Commercially Available Samples:

Comparison 1: sodium carbonate, chem. pure, anhydrous, pulverulent, Ph. Eur., NF, FCC, E500, #1034, batch: RBA0290700, Chemische Fabrik Lehrte Dr. Andreas Kossel GmbH, D-Lehrte/Germany Comparison 2: sodium carbonate IPH, batch: DOC2040821, Ph. Eur., Solvay Chemicals International, Dombasle plant, F-Dombasle/France Example 1: product according to the invention after drying in a vacuum contact dryer (cone-and-screw dryer)

Example 2: product according to the invention after drying in a fluidised-bed dryer

TABLE 1

Bulk density, tapped density, angle of repose:

|  | Bulk density (g/ml) | Tapped density (g/ml) | Angle of repose (degrees) |
|---|---|---|---|
| Comp. 1 | 0.721 | 0.906 | 33.0 |
| Comp. 2 | 0.656 | 0.838 | 36.7 |
| Ex. 1 | 1.066 | 1.208 | 30.5 |
| Ex. 2 | 1.122 | 1.276 | 31.0 |

TABLE 2

Content, drying loss, TGA (thermogravimetry):

|  | Content (% by weight) | Drying loss (% by weight) | TGA (% by weight) |
|---|---|---|---|
| Comparison 1 | 98.3 | 1.4 | 1.037 |
| Comparison 2 | 98.6 | 1.3 | 1.117 |
| Example 1 | 99.8 | 0.12 | 0.065 |
| Example 2 | 99.7 | 0.20 | 0.161 |

TABLE 3

Surface area and pore volume, determined by the BET method, total cumulative pore volume and pore diameter, determined by mercury intrusion

| | BET surface area ($m^2/g$) | BET pore volume ($cm^3/g$) | Total cumulative vol. ($mm^3/g$) | Average pore diameter (Å) |
|---|---|---|---|---|
| Comp. 1 | 2.34 | ~0.0079 | 353 | 4138 |
| Comp. 2 | 2.22 | ~0.0067 | 330 | 4068 |
| Example 1 | ~0.09 | ~0.0008 | 151 | 56 |
| Example 2 | ~0.12 | ~0.0013 | 85 | 38 |

TABLE 4

DVS measurement (dynamic vapour sorption):

Relative humidity (%)

| | 0.0 | 10.0 | 20.0 | 30.0 | 40.0 | 50.0 | 60.0 | 70.0 | 80.0 | 90.0 | 98.0 |
|---|---|---|---|---|---|---|---|---|---|---|---|
| Comp. 1 | 0.0 | 0.0 | 0.0 | 0.1 | 0.1 | 1.0 | 10.3 | 14.9 | 29.9 | 60.0 | 111.7 |
| Comp. 2 | 0.0 | 0.0 | 0.1 | 0.1 | 0.1 | 0.7 | 10.8 | 16.1 | 31.2 | 68.4 | 112.1 |
| Ex. 1 | 0.0 | 0.0 | 0.0 | 0.0 | 0.0 | 0.0 | 1.2 | 3.4 | 8.5 | 30.4 | 71.0 |
| Ex. 2 | 0.0 | 0.0 | 0.0 | 0.0 | 0.0 | 0.0 | 1.3 | 2.7 | 10.0 | 46.7 | 79.0 |

TABLE 5

Particle size distribution (determined via laser diffraction with dry and wet dispersion):
Data in μm Pressure

| | 1 bar dry meas. | | | | 2 bar dry m. | | | | 3 bar dry m. | | | | Wet measurement in EtOH | | | |
|---|---|---|---|---|---|---|---|---|---|---|---|---|---|---|---|---|
| Sample | D(25) | D(50) | D(75) | D(90) | D(25) | D(50) | D(75) | D(90) | D(25) | D(50) | D(75) | D(90) | D(25) | D(50) | D(75) | D(90) |
| Comp. 1 | 69 | 105 | 147 | 190 | 42 | 83 | 126 | 171 | 25 | 74 | 120 | 159 | 62 | 99 | 130 | 172 |
| Comp. 2 | 52 | 83 | 122 | 165 | 28 | 63 | 104 | 149 | 17 | 52 | 95 | 140 | 68 | 96 | 134 | 176 |
| Ex. 1 | 279 | 370 | 490 | 616 | 286 | 387 | 518 | 655 | 267 | 373 | 509 | 650 | 339 | 447 | 587 | 733 |
| Ex. 2 | 360 | 470 | 612 | 762 | 332 | 448 | 597 | 751 | 269 | 389 | 538 | 692 | 283 | 375 | 495 | 620 |

TABLE 6

Particle size distribution (determined via tower sieving):
Data in % by weight

| Sample | <32 μm | 32-50 μm | 50-75 μm | 75-100 μm | 100-150 μm | 150-200 μm | 200-250 μm | 250-300 μm | 300-355 μm |
|---|---|---|---|---|---|---|---|---|---|
| Comp. 1 | 4.5 | 5.7 | 15.3 | 26.6 | 45.2 | 2.0 | 0.1 | 0.1 | 0.1 |
| Comp. 2 | 3.6 | 12.5 | 29.0 | 24.2 | 29.8 | 0.2 | 0.1 | 0.1 | 0.1 |
| Ex. 1 | 0.0 | 0.1 | 0.2 | 0.5 | 7.2 | 11.9 | 15.9 | 17.6 | 16.2 |
| Ex. 2 | 0.0 | 0.0 | 0.1 | 0.1 | 2.2 | 5.9 | 10.7 | 17.6 | 14.7 |

| Sample | 355-400 μm | 400-500 μm | 500-600 μm | 600-710 μm | >710 μm |
|---|---|---|---|---|---|
| Comp. 1 | 0.1 | 0.1 | 0.1 | 0.1 | 0.0 |
| Comp. 2 | 0.1 | 0.1 | 0.1 | 0.1 | 0.0 |
| Ex. 1 | 9.6 | 15.2 | 4.7 | 0.7 | 0.2 |
| Ex. 2 | 10.7 | 20.6 | 11.4 | 4.5 | 1.5 |

It can also be seen in corresponding SEM photographs (see SEM photographs (2500×) FIG. 1-4) that sodium carbonate prepared in accordance with the invention (Examples 1 and 2) has a significantly more compact (low-pore) surface structure than commercially available products (Comparison 1 and 2). While the materials prepared in accordance with Examples 1 and 2 (FIGS. 3 and 4) have very compact surfaces, porous structures are clearly evident in the surfaces of comparative materials 1 and 2 (FIGS. 1 and 2).

Figure 1:
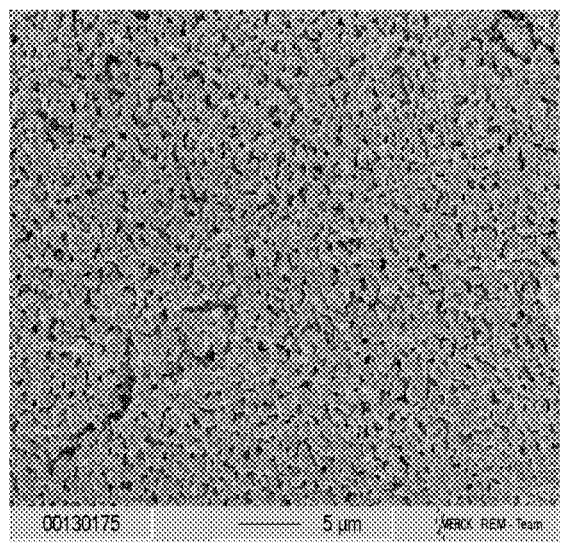
FIG. 1: SEM photograph (2500×) of sodium carbonate, chemically pure, anhydrous, pulverulent, Ph.Eur., NF, FCC, E500, #1034, batch RBA0290700, Chemische Fabrik Lehrte Dr. Andreas Kossel GmbH, D-Lehrte/Germany
Figure 2:
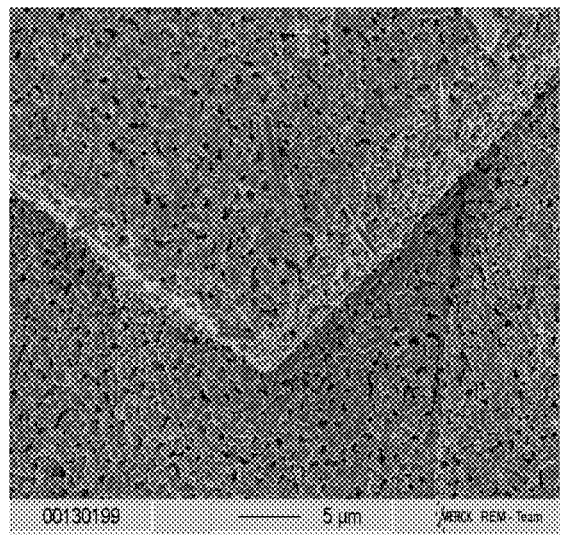
FIG. 2: SEM photograph (2500×) of sodium carbonate IPH, batch: DOC2040821, Ph. Eur., Solvay Chemicals International, Dombasle/France
Figure 3:
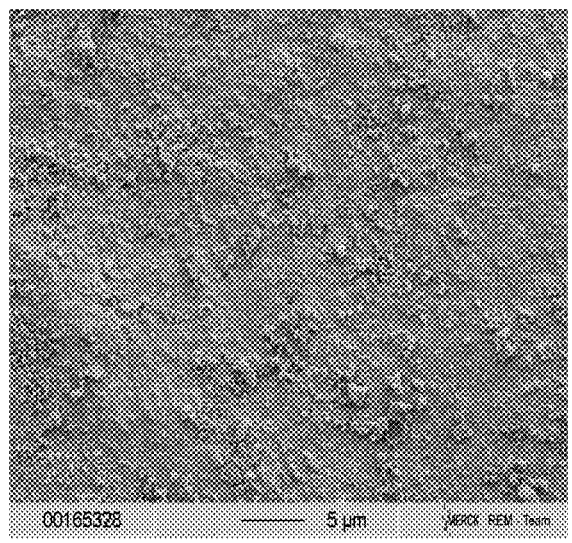
FIG. 3: SEM photograph (2500×) of a sample of an anhydrous sodium carbonate prepared in accordance with the invention according to Example 1
Figure 4:
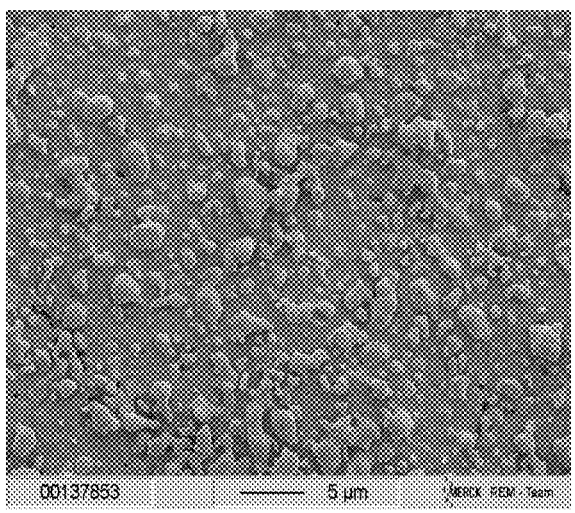
FIG. 4: SEM photograph (2500) of a sample of an anhydrous sodium carbonate prepared in accordance with the invention according to Example 2

The invention claimed is:
1. Crystalline sodium carbonate, which crystalline sodium carbonate:
   is an anhydrous product,
   is a highly pure product shown by a sodium carbonate content of not less than 99.5% determined acidimetrically,
   consists of particles having a smooth surface structure and a low pore content shown by a BET pore volume of about 0.0013 cm$_3$/g or less,
   has a drying loss after preparation of not more than 0.2% by weight, and
   has a BET surface area of less than 1 m$^2$/g.
2. Crystalline sodium carbonate according to claim 1, which
   has a BET surface area of less than 0.5 m$^2$/g,
   and
   has a drying loss after preparation of less than 0.15% by weight.
3. Crystalline sodium carbonate according to claim 1, which has a water vapour absorption capacity (WVAC) of <5% by weight at 60% relative humidity; <10% by weight at 70% relative humidity; <15% by weight at 80% relative humidity and <50% at 90% relative humidity.
4. Crystalline sodium carbonate according to claim 1, which has a bulk density in the range from 1.050 to 1.140 g/ml, a tapped density in the range from 1.18 to 1.30 g/ml and an angle of repose in the range from 30.0° to 31.5°.
5. Process for the preparation of crystalline sodium carbonate according to claim 1, which comprises:
   preparing an aqueous solution in which sodium hydrogencarbonate and sodium hydroxide solution are dissolved in an amount such that the solution has a density in the range from 1.2 to 1.4 g/ml at 65° C. and sodium hydrogencarbonate (NaHCO$_3$) and sodium hydroxide solution (NaOH) are present therein in a molar ratio of 1:1 to 1:1.3,
   subsequently, successively adding a catalytic amount of hydrogen peroxide and activated carbon to the solution, which is then filtered after mixing,
   feeding the clear solution obtained from the previous step to a crystallisation apparatus, in which liquid is removed by vacuum evaporation and a suspension density in the range from 1.54-1.86 g/ml is set at which the crystallisation is carried out,
   separating off the crystals formed in the previous step by filtration, centrifugation or spinning-off, and
   introducing the crystals into a dryer and drying them with continuous mixing until the product obtained has a drying loss of not more than 0.2% by weight.
6. Process according to claim 5, wherein the process is carried out in a loop crystalliser.
7. Process according to claim 5, wherein the process is carried out batchwise.
8. Process according to claim 5, wherein the temperature during the crystallisation is set in the range from 50 to 95° C., while the density of the suspension is in the range from 1.54-1.86 g/ml.
9. Process according to claim 5, wherein the aqueous solution is mixed with 30% hydrogen peroxide in a ratio of 700:1 to 900:1, based on the weight of the entire solution, and with activated carbon in a ratio of 20000:1 to 10000:1, based on the weight of the entire solution.
10. Process according to claim 5, wherein the crystallisation is carried out at a temperature in the range from 70 to 90° C. and a suspension density in the range from 1.62-1.78 g/ml.
11. Process according to claim 5, wherein the crystallisation is carried out at a temperature in the range from 50 to 60° C., and a suspension density in the range from 1.72 to 1.75 g/ml.
12. Process according to claim 5, wherein,
   for the separating off and drying of the crystals, the crystals are fed to a screen centrifuge by means of a mixer screw, washed with water and introduced into a mixer dryer via a flow dryer and dried at a temperature of 115 to 125° C. with continued mixing until the product obtained has a drying loss of less than 0.2% by weight,
   or
   after spinning-off, the crystals are fed to a fluidised-bed dryer via a screw conveyor and dried at a temperature in the range from 175 to 200° C., with a residence time, so that the product obtained has a drying loss of not more than 0.2% by weight.
13. A composition comprising crystalline carbonate according to claim 1, optionally after prior grain classification by sieving or grinding, in the form of a solid pharmaceutical formulation.
14. An effervescent formulation comprising vitamins and/or mineral substances and/or trace elements and/or hydrolysis-sensitive active compounds and crystalline sodium carbonate of claim 1.
15. A tablet, granule or effervescent formulation comprising acidic active compounds and/or hydrolysis-sensitive active compounds and crystalline sodium carbonate of claim 1.
16. A composition of claim 13, wherein the composition is in the form of a tablet, capsule, powder or granule.
17. Crystalline sodium carbonate, according to claim 1, which has a drying loss after preparation of not more than 0.15% by weight.
18. Crystalline sodium carbonate according to claim 1, which has a BET surface area of less than 0.2 m$^2$/g.
19. The process according to claim 5, wherein: the aqueous solution has a density in the range from 1.25 to 1.34 g/ml.
20. The process according to claim 5, wherein: the aqueous solution has a density in the range from 1.28 to 1.31 g/ml.
21. The process according to claim 5, wherein: a suspension density in the range from 1.58-1.82 g/ml is set at which the crystallisation is carried out.
22. The process according to claim 5, wherein: a suspension density in the range from 1.62-1.78 g/ml is set at which the crystallisation is carried out.
23. Process according to claim 5, wherein the process is carried out continuously.
24. Process according to claim 5, wherein the temperature during the crystallisation is set in the range from 55 to 90° C.
25. Process according to claim 5, wherein the aqueous solution is mixed with 30% hydrogen peroxide in a ratio of 800:1 to 760:1, based on the weight of the entire solution, and with activated carbon in a ratio of 16500:1 to 14000:1, based on the weight of the entire solution.
26. Process according to claim 5, wherein the crystallisation is carried out at a temperature of 55° C.
27. Process according to claim 5, wherein, after spinning-off, the crystals are fed to a fluidised-bed dryer via a screw conveyor and dried at a temperature in the range from 180 to

195° C., with a residence time, so that the product obtained has a drying loss of not more than 0.2% by weight.

28. A composition of claim 13, wherein the composition is in the form of a capsule suitable for oral administration.

* * * * *